United States Patent [19]

Lawson

[11] Patent Number: 4,695,278

[45] Date of Patent: Sep. 22, 1987

[54] ABSORBENT ARTICLE HAVING DUAL CUFFS

[75] Inventor: Michael I. Lawson, Cincinnati, Ohio

[73] Assignee: The Procter & Gamble Company, Cincinnati, Ohio

[21] Appl. No.: 786,926

[22] Filed: Oct. 11, 1985

[51] Int. Cl.$^4$ .............................................. A61F 13/16
[52] U.S. Cl. ................................................. 604/385 A
[58] Field of Search ................. 604/385.1, 385.2, 394, 604/396, 397, 398, 389

[56] References Cited

U.S. PATENT DOCUMENTS

| | | |
|---|---|---|
| 2,545,674 | 3/1951 | Ralph . |
| 2,575,164 | 11/1951 | Donovan . |
| 2,916,037 | 12/1959 | Hansen . |
| 3,386,442 | 6/1968 | Sabee ............................ 128/287 |
| 3,530,859 | 9/1970 | Helmowitz . |
| 3,572,342 | 3/1971 | Lindquist et al. . |
| 3,658,064 | 4/1972 | Pociluyko . |
| 3,744,494 | 7/1973 | Marsan . |
| 3,807,402 | 4/1974 | Miller et al. . |
| 3,860,003 | 1/1975 | Buell . |
| 3,920,017 | 11/1975 | Karami ............................ 128/287 |
| 3,929,134 | 12/1975 | Karami . |
| 3,978,861 | 9/1976 | Schaar . |
| 3,999,548 | 12/1976 | Hernandez . |
| 4,040,423 | 8/1977 | Jones, Sr. .......................... 604/385.2 |
| 4,041,950 | 8/1977 | Jones, Sr. . |
| 4,090,515 | 10/1985 | Karami . |
| 4,319,572 | 3/1982 | Widlund et al. . |
| 4,326,528 | 4/1982 | Ryan et al. . |
| 4,430,086 | 2/1984 | Repke ............................... 604/385 |
| 4,490,148 | 12/1984 | Beckestrom ....................... 604/385 |
| 4,496,360 | 1/1985 | Joffe et al. ......................... 604/397 |
| 4,500,316 | 2/1985 | Damico ............................. 604/389 |

FOREIGN PATENT DOCUMENTS 4521785 2/1986 Australia .
2159693 12/1985 United Kingdom .
2161059 1/1986 United Kingdom .

Primary Examiner—John D. Yasko
Attorney, Agent, or Firm—Steven W. Miller; John M. Pollaro; Richard C. Witte

[57] ABSTRACT

An integral disposable absorbent article such as a diaper having a liquid pervious topsheet, a liquid impervious backsheet, an absorbent core disposed between the topsheet and the backsheet, at least one elastically contractible gasketing cuff, and at least one barrier cuff. The barrier cuff has a proximal edge and a distal edge. The absorbent article is additionally provided with spacing means for spacing the distal edge away from the top surface of the topsheet. In addition, adhesive means secure the end portions of the barrier cuff closed. A channel is formed between the proximal and distal edges in at least the crotch region because the distal edge is spaced away from the topsheet top surface.

When the diaper embodiment of the present invention is applied to a wearer, the barrier cuff rides up along the inner thighs and the perineum of the wearer in the crotch region and along the buttocks in the back waist region. Leakage prevention is enhanced because body exudates which are not immediately absorbed by the absorbent core contact the barrier cuff and are contained and held within the channel so that they do not wick out of the diaper or flow out of the gaps between the diaper and the legs or waist of the wearer. Additionally, should such exudates flow beyond the barrier cuff, leakage is further enhanced by the gasketing cuff because it forms an additional liquid impervious barrier about the leg or waist of the wearer.

28 Claims, 7 Drawing Figures

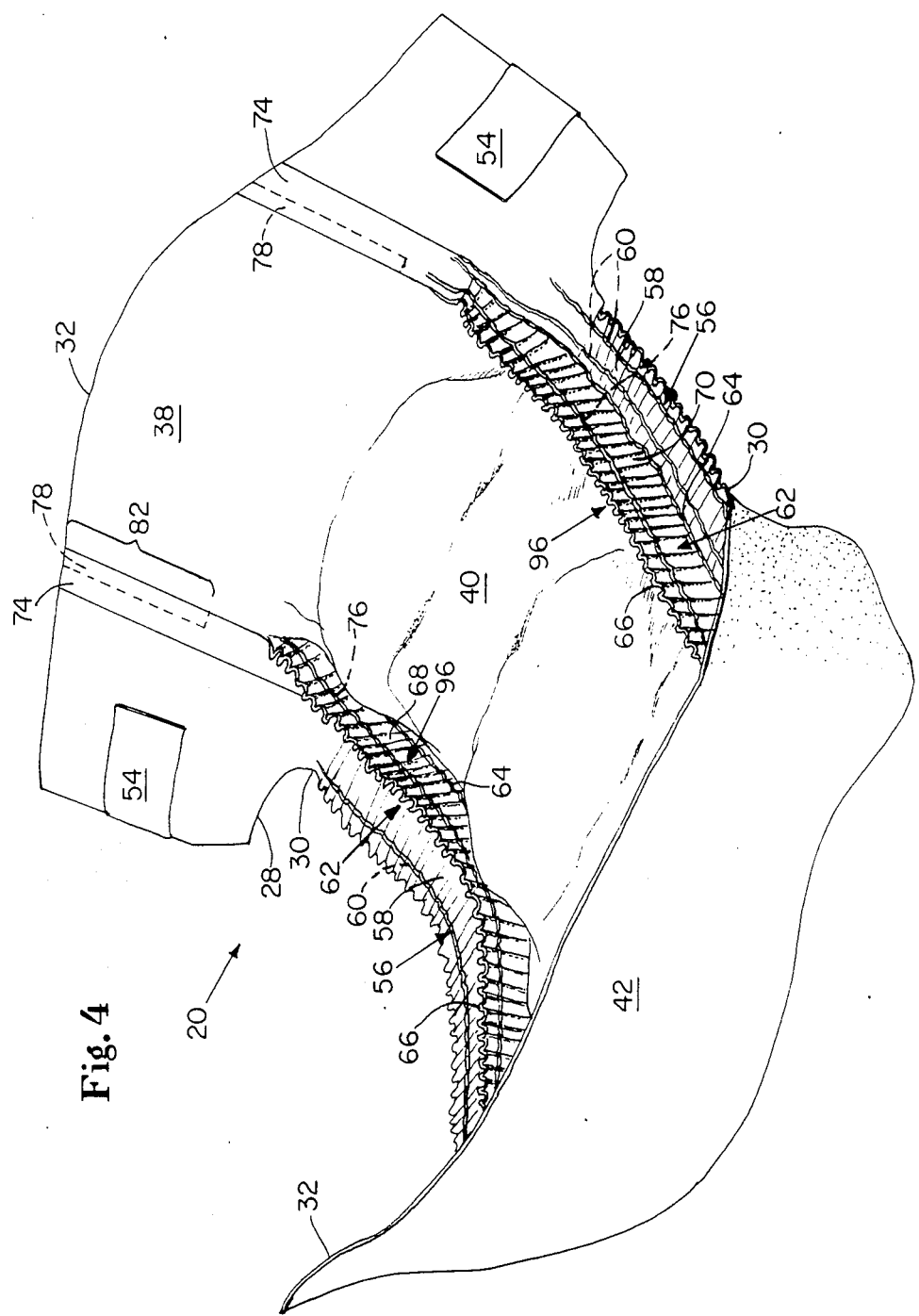

ABSORBENT ARTICLE HAVING DUAL CUFFS

FIELD OF THE INVENTION

The present invention relates to absorbent articles such as disposable diapers, and more particularly, to absorbent articles having a gasketing cuff and a barrier cuff which improve the containment characteristics of the article.

BACKGROUND OF THE INVENTION

The major function of absorbent articles such as disposable diapers and adult incontinent briefs, is to absorb and contain body exudates. Such articles are also intended to prevent body exudates from soiling, wetting, or otherwise contaminating clothing or other articles, such as bedding, that come in contact with the wearer. The most common mode of failure for such products occurs when body exudates leak out of the gaps between the article and the wearer's leg or waist to adjacent clothing because they are not immediately absorbed within the article. This is most evident with loose fecal material which is not easily absorbed by the absorbent article and tends to "float" on the top surface of the absorbent article.

Contemporary disposable diapers, such as those disclosed in U.S. Pat. No. 3,860,003 issued to Kenneth Barclay Buell on Jan. 14, 1975, have topsheet, a backsheet, an absorbent core, and elasticized leg flaps to improve both wearing comfort and the ability to contain body exudates. These elasticized leg flaps prove effective generally to prevent wicking and overflow from the fluid laden diaper to clothing contacting the edges of the diaper in that the elasticized leg flaps present a liquid impervious barrier between the edge of the diaper and the contacting clothing, and in addition, provide a gasketing action about the legs of the wearer. Despite the effectiveness of such structures, however, body exudates, especially loose fecal material, can leak through the elasticized leg flaps and soil the wearer's clothing because the diaper does not constrain the free flow of such material nor provide a structure to hold it within the diaper so that as such material freely floats on the top surface of the topsheet, it tends to work its way past the elasticized leg flaps.

Therefore, it is an object of the present invention to provide an absorbent article which has improved containment characteristics.

It is an additional object of the present invention to provide an absorbent article having a barrier cuff which acts as a restraint against the leakage of body exudates.

It is a further object of the present invention to provide an absorbent article having an elastically contractible gasketing cuff and a barrier cuff so as to provide a dual restraint against the leakage of body exudates, thereby improving the containment characteristics of the absorbent article, especially in regard to loose fecal material.

It is also an object of the invention to provide an absorbent article having a barrier cuff that is raised above the top surface of the topsheet when the article is fitted on the wearer such that a channel is formed which constrains and holds body exudates within the article.

These and other objects of the invention will be more readily apparent when considered in reference to the following description and when taken in conjunction with the accompanying drawings.

SUMMARY OF THE INVENTION

In accordance with the present invention, an integral disposable absorbent article such as a diaper is provided with a liquid pervious topsheet, a liquid impervious backsheet, an absorbent core disposed between the topsheet and the backsheet, at least one elastically contractible gasketing cuff, and at least one barrier cuff. The barrier cuff has a proximal edge and a distal edge. The absorbent article is additionally provided with spacing means for spacing the distal edge away from the top surface of the topsheet. In addition, adhesive means secure the end portions of the barrier cuffs closed. A channel is formed between the proximal edge and the distal edge in at least the crotch region because the distal edge is spaced away from the topsheet top surface.

When a diaper embodiment of the present invention is applied to a wearer, the barrier cuff rides up along the inner thigh and the perineum of the wearer in the crotch region and along the buttocks in the back waist region. Leakage prevention is enhanced because body exudates which are not immediately absorbed by the absorbent core, typically loose fecal material, contact the barrier cuff and are contained and held within the channel so that they do not leak out of the diaper at the gaps between the diaper and the legs or waist of the wearer. Additionally, should such exudates flow beyond the barrier cuff, leakage is further enhanced by the gasketing cuff because it forms an additional liquid impervious barrier about the leg or waist of the wearer.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

FIG. 4 is a perspective view of the disposable diaper embodiment of FIG. 1.

DETAILED DESCRIPTION OF THE INVENTION

Figure 1:
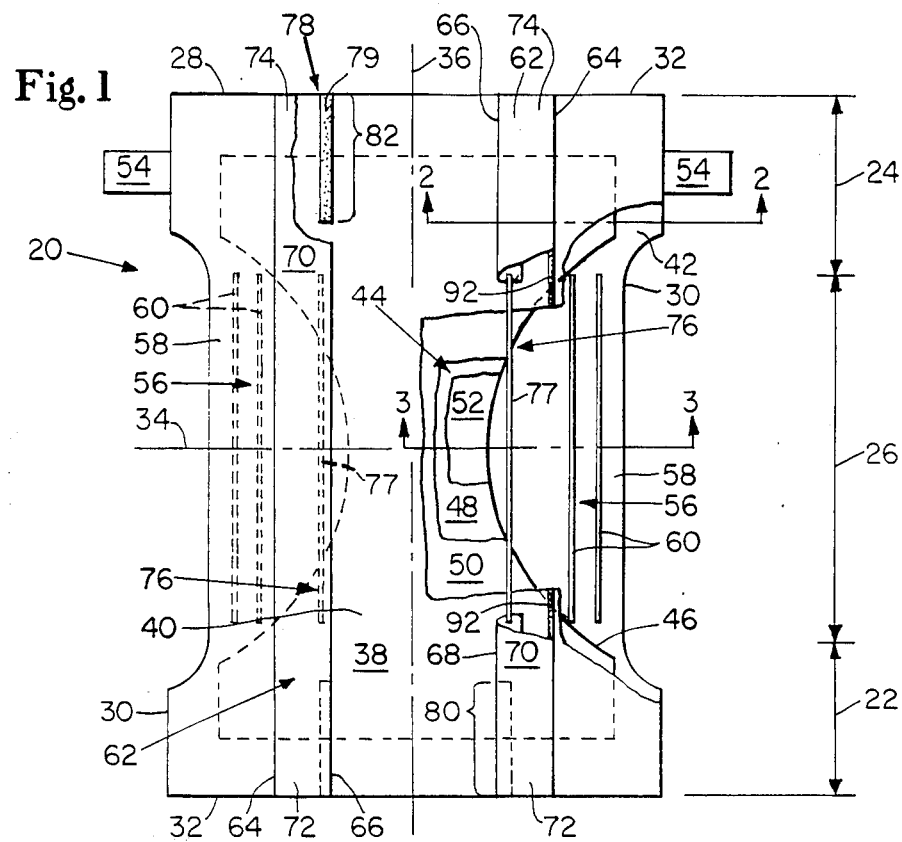
FIG. 1 is a plan view of a disposable diaper embodiment of the present invention having portions cut away to reveal underlying structure.

As used herein, the term "integral disposable absorbent article" refers to articles which absorb and contain body exudates and more specifically refers to articles which are placed against or in proximity to the body of the wearer to absorb and contain the various exudates discharge from the body, and which are intended to be discarded after a single use (i.e., they are not intended to be laundered or otherwise restored or reused), and which are unitary in that they do not require separate manipulative parts like a separate holder and liner. A preferred embodiment of the integral disposable absorbent article of the present invention, diaper 20, is shown in FIG. 1. As used herein, the term "diaper" refers to a garment generally worn by infants and incontinent persons that is worn about the lower torso of the wearer. It should be understood, however, that the present invention is also applicable to other integral disposable articles such as incontinent briefs and the like.

FIG. 1 is a plan view of the diaper 20 of the present invention in its flat-out, uncontracted state (i.e., with all elastic induced contraction pulled out) with portions of the structure being cut away to more clearly show the construction of the diaper 20 and with the portion of the diaper 20 which contacts the wearer facing the viewer. The diaper 20 is shown in FIG. 1 to have a front waist region 22, a back waist region 24, a crotch region 26 and a periphery 28 which is defined by the outer edges of the diaper in which the longitudinal edges are designated 30 and the end edges are designated 32. The diaper 20 additionally has a lateral centerline which is designated 34 and a longitudinal centerline which is designated 36.

The diaper 20 comprises a liquid pervious topsheet 38, the top surface of the topsheet 38 being designated 40; a liquid impervious backsheet 42; an absorbent core 44 having side edges 46 and comprising an abosrbent layer 48 and first and second tissue layers 50 and 52, respectively; a pair of tape-tab fasteners 54; gasketing cuffs 56 each comprising a side flap 58 and flap elastic members 60; barrier cuffs 62 each having a proximal edge 64, a distal edge 66, an inboard surface 68, an outboard surface 70, a first end 72 and a second end 74; and spacing means 76 such as spacing elastic member 77 for spacing the distal edge 66 away from the topsheet top surface 40. The diaper 20 additionally comprises adhesive means 78 such as a glue bead 79 for securing closed the first and second ends 72 and 74 of each barrier cuff 62. The areas in which the adhesive means 78 are disposed are designated front closure zone 80 and back closure zone 82. While the topsheet 38, the absorbent core 44, the backsheet 42, and the elastically contractible gasketing cuffs 56 may be assembled in a variety of well known configurations, a preferred diaper configuration is described generally in U.S. Pat. No. 3,860,003 entitled "Contractable Side Portions for Disposable Diaper", which issued to K. B. Buell on Jan. 14, 1975, and which patent is incorporated herein by reference.

FIG. 1 shows a preferred embodiment of the diaper 20 in which the topsheet 38 and the backsheet 42 are coextensive and have length and width dimensions generally larger than those of the absorbent core 44. The topsheet 38 is associated with and superposed on the backsheet 42 to thereby form the periphery 28 of the diaper 20. The periphery 28 defines the outer periper or, in other words, the edges of the diaper 20. The periphery 28 comprises the end edges 32 and the longitudinal edges 30.

The diaper 20 has front and back waist regions 22 and 24 extending, respectively, from the end edges 32 of the diaper periphery 28 toward the lateral centerline 34 of the diaper 20 a distance from about ¼ to about ⅓ the length of the diaper 20. The waist regions comprise those portions of the diaper 20 which, when worn, encircle the waist of the wearer. The crotch region 26 is that portion of the diaper 20 between the waist regions 22 and 24, and comprises that portion of the diaper 20 which, when worn, is positioned between the legs of the wearer and covers the lower torso of the wearer.

Figure 2:
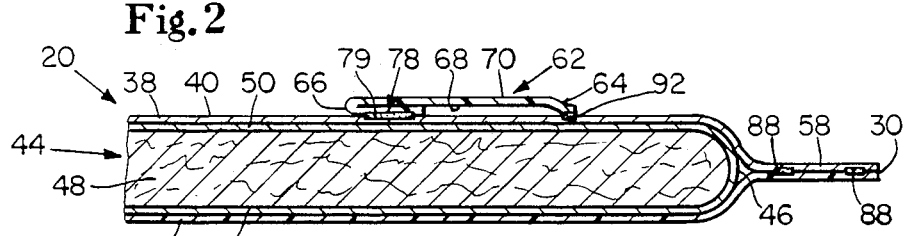
FIG. 2 is a fragmentary sectional view taken along section line 2—2 of FIG. 1.

FIG. 2 is a fragmentary sectional view taken along line 2—2 of FIG. 1 and depicts the diaper construction in the back waist region 24 of the diaper 20. (It should be understood that the diaper construction in the front waist region 22 is identical to the construction in the back waist region 24.) The absorbent core comprises the absorbent layer 48 that is shown as being completely enveloped by the first and second tissue layers 50 and 52. The absorbent core 44 is disposed between the topsheet 38 and the backsheet 42; both the topsheet 38 and the backsheet 42 extend beyond the side edge 46 of the absorbent core 44 to define the side flap 58. The juxtaposed areas of the topsheet 38 and the backsheet 42 are adhesively secured together by adhesive 88. In a preferred embodiment, the flap elastic members 60 do not extend into the front waist region 22 so that the gasketing cuff 56 is not formed in this region. The barrier cuff 62 is shown as being a separate element secured to the topsheet 38; the proximal edge 64 being formed by securing the element to the topsheet 38 by adhesive 92. The inboard surface 68 of the barrier cuff 62 is secured to the topsheet top surface 40 by adhesive means 78 such as the glue bead 79. Therefore, the distal edge 66 is closed. (i.e., it is not spaced away from the topsheet top surface 40). It should be noted that the spacing elastic member 77 is not disposed in this region because the distal edge 66 is not designed to be spaced away from the topsheet top surface 40 in the waist regions. Therefore, the barrier cuff 62 is not open nor ready to constrain the flow of body exudates in this region.

Figure 3:
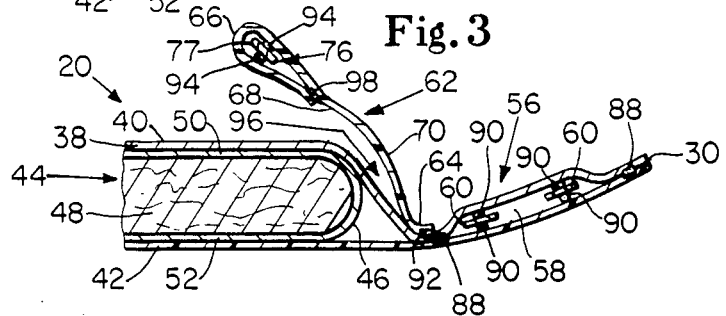
FIG. 3 is a fragmentary sectional view taken along section line 3—3 of FIG. 1.

FIG. 3 is a fragmentary sectional view taken along line 3—3 of FIG. 1 and depicts the diaper construction in the crotch region 26 of the diaper 20 as it is shaped before being applied to the wearer (i.e., the diaper 20 is subjected to elastic contraction). The absorbent core 44 comprises the absorbent layer 48 that is shown as being completely enveloped by the first and second tissue layers 50 and 52. The absorbent core 44 is disposed between the topsheet 38 and the backsheet 42; both the topsheet 38 and the backsheet 42 extend beyond the side edge 46 of the absorbent core 44 to define the side flap 58. The juxtaposed areas of the topsheet 38 and the backsheet 42 are adhesively secured together by adhesive 88. The topsheet 38 and the backsheet 42 also enclose the flap elastic members 60 adjacent the longitudinal edge 30 in the periphery 28. The flap elastic members 60 are secured in the topsheet-backsheet formed side flap 58 by elastic attachment means 90. The elastically contractible gasketing cuff 56 is thereby formed by the side flap 58 and the flap elastic members 60. The barrier cuff 62 is shown as being formed by securing an element to the topsheet 38 between the flap elastic members 60 and the side edge 46 of the absorbent core 44. The proximal edge 64 of the barrier cuff 62 is formed by securing the barrier cuff element to the topsheet 38 by adhesive 92. The spacing elastic members 77 are enclosed in a tunnel that is formed when an end of the barrier cuff element is folded back upon itself; the spacing elastic members 77 being secured in the barrier cuff 62 by elastic attachments means 94. The distal edge 66 of the barrier cuff is spaced away from the topsheet top surface 40 by the elastic gathering action of the spacing elastic members 77; a channel 96 thereby being formed by at least the proximal edge 64, the distal edge 66 and the inboard surface 68 of the barrier cuff 62. The channel 96 is shown as being ready to restrain, contain and hold body exudates until the diaper 20 is removed from the wearer.

The topsheet 38 is compliant, soft feeling, and non-irritating to the wearer' skin. Further, the topsheet 38 is liquid pervious permitting liquids to readily penetrate through its thickness. A suitable topsheet may be manufactured from a wide range of materials, such as porous foams, reticulated foams, apertured plastic films, natural fibers (e.g., wood or cotton fibers), synthetic fibers (e.g., polyester or polypropylene fibers) or from a combination of natural and synthetic fibers. Preferably, it is made of a hydrophobic material to isolate the wearer's skin from liquid in the absorbent core 44.

A particularly preferred topsheet 38 comprises staple length polypropylene fibers having a denier of about 1.5, such as Hercules Type 151 polypropylene marketed by Hercules, Inc. of Wilmington, Del. As used herein, the term "staple length fibers" refers to those fibers having a length of at least about 15.9 mm (0.625 inches).

There are a number of manufacturing techniques which may be used to manufacture the topsheet 38. For example, the topsheet 38 may be woven, non-woven, spunbonded, carded, or the like. A preferred topsheet 38 is carded, and thermally bonded by means well known to those skilled in the fabrics art. Preferably, the topsheet 38 has a weight from about 18 to about 25 grams per square meter, a minimum dry tensile strength of at least about 400 grams per centimeter in the machine direction and a wet tensile strength of at least about 55 grams per centimeter in the cross machine direction.

The absorbent core 44 may be any means which is generally compressible, conformable, non-irritating to the wearer's skin, capable of absorbing and retaining fluids and certain body exudates. A preferred absorbent core 44 has first and second opposed faces and comprises an absorbent layer 48 and first and second tissue layers 50 and 52, respectively. The first and second tissue layers 50 and 52 overlay the major surfaces of the absorbent layer 48 to form the first and second opposed faces of the absorbent core.

The absorbent layer 48 may be manufactured in a wide variety of sizes and shapes (e.g., rectangular, hourglass, etc.) and from a wide variety of liquid absorbent materials commonly used in disposable diapers and other absorbent articles, such as comminuted wood pulp which is generally referred to as airfelt. Examples of other suitable absorbent materials include creped cellulose wadding, absorbent foams, absorbent sponges, super absorbent polymers, or any equivalent material or combination of materials. The total absorbent capacity of the absorbent layer 84 should, however, be compatible with the design exudate loading in the intended use of the diaper 20. Further, the size and absorbent capacity of the absorbent layer 48 may be varied to accommodate wearers ranging from infants through adults.

A preferred embodiment of the diaper 20 shown in FIG. 1 has an hourglass shaped absorbent layer 48 and is intended to be worn by infants ranging in weight from about 5 kgs to about 12 kgs (about 12 pounds to about 26 pounds). The airfelt used in the absorbent layer 48 weighs from about 30 grams to about 56 grams, has a generally uniform caliper, and has an absorbent capacity of from about 8 grams to about 16 grams of water per gram of absorbent material. It should be understood, however, that the size, shape, configuration, and total absorbent capacity of the absorbent layer 48 may be varied to accommodate wearers ranging from infants through adults. Therefore, the dimensions, shape, and configuration of the absorbent layer 48 may be varied (e.g., the absorbent layer may have a varying caliper, or a hydrophillic gradient, or may contain superabsorbent materials). The absorbent layer is preferably, therefore, a batt of airfelt about 32 cm wide (lateral dimensions), about 45 cm long (longitudinal dimension) and approximately 7 cm across the narrowest part of the crotch region.

The first and second tissue layers 50 and 52 improve the tensile strength of the absorbent core 44 and reduce the tendency of the absorbent layer 48 to split, lump or ball when wetted. The first and second tissue layers 50 and 52 also help to improve lateral wicking of the absorbed exudates, thereby providing a more even distribution of the exudates throughout the absorbent layer 48. While a number of materials and manufacturing techniques may be used to manufacture the first and second tissue layers 50 and 52, satisfactory results have been obtained with sheets of tissue paper having a basis weight of about 16 grams per square meter (10 lbs. per 3000 square feet) and having an air permeability of about 30.5 cubic meters per minute per square meter (100 cubic feet per minute per square foot) at a pressure differential of about 12.8 millimeters of water ($\frac{1}{2}$ inch). While the first and second tissue layers 50 and 52 are preferably coterminous with the absorbent layer 48, they may have different dimensions, a different configuration, or they may be omitted entirely.

The absorbent core 44 is superimposed on the backsheet 42 and is preferably attached thereto by attachments means (not shown) such as those well known in the art. For example, the absorbent core 44 may be secured to the backsheet 42 by a uniform continuous layer of adhesive, a patterned layer of adhesive, or an array of separate lines or spots of adhesive. An adhesive which has been found to be satisfactory is manufactured by Eastman Chemical Products Company of Kingsport, Tenn. and marketed under the tradename Eastobond A-3.

The backsheet 42 is impervious to liquids and is preferably manufactured from a thin plastic film, although other flexible liquid impervious materials may also be used. The backsheet 42 prevents the exudates absorbed and contained in the absorbent core 44 from wetting articles which contact the diaper 20 such as bedsheets and undergarments. Preferably, the backsheet 42 is a polyethylene film having a thickness of from about 0.012 mm (0.5 mil) to about 0.051 cm (2.0 mils), although other flexible, liquid impervious materials may be used. As used herein, the term "flexible" refers to materials which are compliant and which will readily conform to the general shape and contours of the human body.

A suitable polyethylene film is manufactured by Monsanto Chemical Corporation and marketed in the trade as Film No. 8020. The backsheet 42 is preferably embossed and/or matte finished to provide a more clothlike appearance. Further, the backsheet 42 may permit vapors to escape from the absorbent core 44 while still preventing exudates from passing through the backsheet 42.

The size of the backsheet 42 is dictated by the size of absorbent core 44 and the exact diaper design selected. In a preferred embodiment, the backsheet 42 has a modified hourglass shape extending beyond the absorbent core 44 a minimum distance of at least about 1.3 cm to about 2.5 cm (about 0.5 to about 1.0 inch) around the entire diaper periphery 28.

The topsheet 38 and the backsheet 42 are associated together in any suitable manner. As used herein, the term "associated" encompasses configurations whereby the topsheet 38 is directly joined to the backsheet 43 by affixing the topsheet 38 directly to the backsheet 42, and configurations whereby the topsheet 38 is indirectly joined to the backsheet 42 by affixing the topsheet 38 to intermediate members which in turn are affixed to the backsheet 42. In a preferred embodiment, the topsheet 38 and the backsheet 42 are joined directly to each other in the diaper periphery 28 by attachment means such as adhesive 88 or any other attachment means as known in the art. For example, a uniform continuous layer of adhesive, a patterned layer of adhesive, or an array of separate lines or spots of adhesive may be used.

Tape tab fasteners 54 are typically applied to the back waist region 24 of the diaper 20 to provide a fastening means to hold the diaper on the wearer. The tape tab fasteners 54 can be any of those well known in the art, such as the fastening tape disclosed in U.S. Pat. No. 3,848,594 issued to K. B. Buell on Nov. 19, 1974, which is incorporated herein by reference. These tape tab fasteners 54 or other diaper fastening means, such as pins, are typically applied near the top edge of a diaper in its "in-use" configuration.

The elastically contractible gasketing cuffs 56 are disposed adjacent the periphery 28 of the diaper 20, preferably along each longitudinal edge 30 so that the gasketing cuffs 56 tend to draw and hold the diaper 20 against the legs of the wearer. Alternatively, a gasketing cuff 56 may be disposed adjacent either or both of the end edges 32 of the diaper 20 to provide a waistcuff rather than leg cuffs. While the gasketing cuffs 56 may comprise any of several means as are well known in the diaper art, a particularly preferred gasketing cuff construction comprises a flexible side flap 58 and a flap elastic member 60, as is described in detail in the hereinbefore referenced U.S. Pat. No. 3,860,003. In addition, a method and apparatus suitable for manufacturing a disposable diaper having elastically contractible gasketing cuffs 56 are described in U.S. Pat. No. 4,081,301 entitled "Method and Apparatus for Continuously Attaching Discrete, Stretched Elastic Strands to Predetermined Isolated Portions of Disposable Absorbent Articles" which issued to K. B. Buell on Mar. 28, 1978 and which patent is incorporated herein by reference.

The side flap 58 should be highly flexible and thus contractible so that the flap elastic members 60 may gather the side flap 58 to provide a gasketing cuff 56 about the legs or waist of the wearer. The side flaps 58 are that portion of the diaper 20 between the periphery 28 and the edges of the absorbent core 44. Thus in a preferred embodiment of the present invention as shown in FIG. 1, the side flaps 58 are formed from the extension of the backsheet 42 and the topsheet 38 from and along the side edges 46 of the absorbent core 44 of the diaper 20 in at least the crotch region 26.

The flap elastic members 60 are secured to the side flaps 58 in an elastically contractible condition so that in a normally unrestrained configuration, the flap elastic members 60 effectively contract or gather the side flaps 58. The flap elastic members 60 can be secured to the side flaps 58 in an elastically contractible condition in at least two ways. For example, the flap elastic members 60 may be stretched and secured to the side flaps 58 while the side flaps 58 are in an uncontracted condition. Alternatively, the side flaps 58 may be contracted, for example by pleating, and the flap elastic members 60 secured to the contracted side flaps 58 while the flap elastic members 60 are in their unrelaxed or unstretched condition.

In the embodiment illustrated in FIG. 1, the flap elastic members 60 extend essentially the entire length of the side flaps 58 in the crotch region 26 of the diaper 20. Alternatively, the elastic members 60 may extend the entire length of diaper 20, or any other length suitable to provide an elastically contractible gasketing cuff. The length of the flap elastic members 60 is dictated by the diaper's design.

In the diaper 20 of FIG. 3, the flap elastic members 60 are associated with the side flaps 58 by securing them to the side flaps 58 with elastic attachments means 90. The elastic attachment means 90 should be flexible and of sufficient adhesiveness to hold the flap elastic member in its stretched condition. The elastic attachment means 90 herein are preferably glue beads made of hot melt adhesives such as marketed by Findley Adhesives Incorporated, Elm Grove, Wis. as Findley Adhesives 581. A more detailed description of the manner in which the flap elastic members 60 may be positioned and secured to the diaper 20 can be found in U.S. Pat. No. 4,253,461 issued to Strickland and Visscher on Mar. 3, 1981, and U.S. Pat. No. 4,081,301 issued to Buell on Mar. 28, 1978, both of which are incorporated herein by reference.

One flap elastic member 60 which has been found to be suitable is an elastic strand having a cross section of 0.18 mm by 1.5 mm and made from natural rubber as available from Easthampton Rubber Thread Company of Stewart, Va., under the trademark L-1900 Rubber Compound. Other suitable flap elastic members 60 can be made from natural rubber, such as elastic tape sold under the trademark Fulflex 9211 by Fulflex Company of Scotland, N.C. The flap elastic member 60 may also comprise any heat shrinkable elastic material as is well known in the art. Other suitable flap elastic members 60 may comprise a wide variety of materials as are well known in the art including elastomeric films, polyurethane films, elastomeric foams, and formed elastic scrim.

In addition, the flap elastic members 60 may take a multitude of configurations. For example, the width of the flap elastic members 60 may be varied from about 0.25 mm (0.01 inches) to about 25 mm (1.0 inch) or more; the flap elastic members 60 may comprise a single strand of elastic material or may comprise several parallel or non-parallel strands of elastic material; or the flap elastic members 60 may be rectilinear or curvilinear. Still further, the flap elastic members 60 may be affixed to the diaper 20 in any of several ways which are well known in the art. For example, the flap elastic members 60 may be ultrasonically bonded, heat/pressure sealed into the diaper 20 using a variety of bonding patterns or the elastic members 60 may simply be glued to the diaper 20.

Each barrier cuff 62 is a flexible member having a proximal edge 64, a distal edge 66, an inboard surface 68 and an outboard surface 70. As used herein, the term flexible refers to materials which are compliant and will readily conform to the general shape and contours of the body. In addition, if the spacing means 76 comprise spacing elastic members 77, the barrier cuff 62 must be contractible so that the distal edge 66 may be sufficiently spaced away from the topsheet top surface 40 so that a channel 96 is formed to restrain, contain and hold body exudates within the article. The barrier cuff 62 may be manufactured from a wide variety of materials such as polypropylene, polyester, rayon, nylon, foams, plastic films, formed films, and elastic foams. A number of manufacturing techniques may be used to manufacture the barrier cuff. For example, the barrier cuff 62 may be woven, non-woven, spunbonded, carded, or the like. A particularly preferred barrier cuff 62 comprises a polypropylene material containing no finish or surfactant to render it liquid impermeable. A particularly preferred polypropylene material is manufactured by Crown Zellerbach Company as Celestra.

As shown in FIGS. 1 and 3, the barrier cuff 62, and more particularly the proximal edge 64, is disposed inboard of and preferably adjacent to the gasketing cuff 32. The term "inboard" is defined as the direction toward the centerline (30 or 32, respectively) of the diaper that is parallel to the respective edge of the diaper 20 along which the particular gasketing cuff 56 is disposed. The barrier cuff 62 is disposed inboard of the gasketing cuff 56 so that exudates, especially loose fecal material which is not easily absorbed and tends to float along the topsheet top surface 40, will contact the barrier cuff 62 before it can contact the gasketing cuff 56. The barrier cuff 62 is disposed adjacent the gasketing cuff 56 to provide a more effective dual restraint against the flow of body exudates. The barrier cuff 62 is preferably disposed between the flap elastic member 60 of the gasketing cuff 56 and the longitudinal centerline 36 of the diaper 20. Most preferably, the barrier cuff 62 is disposed between the flap elastic member 60 and the side edge 46 of the absorbent core 44 in the crotch region 26 of the diaper 20.

The proximal edge 64 and the distal edge 66 are in spaced relation to each other and define the width of the barrier cuff 62. The proximal and distal edges 64 and 66, respectively, may be in a parallel, non parallel, rectilinear or curvilinear relationship. In addition, the barrier cuff 62 may have a variety of different cross sectional areas including circular, square, rectangular or any other shape such as shown in FIG. 3. Preferably, the proximal edge 64 is spaced from the distal edge 66 in a parallel and rectilinear relationship to provide a barrier cuff 62 having uniform widths. Each barrier cuff 62 preferably has a width of at least about 5 mm, and preferably from about 10 mm to about 25 mm.

A preferred embodiment of the diaper 20 shown in FIG. 1 is provided with the barrier cuff 62 joined to the topsheet 38. The term "joined" includes any means for affixing the barrier cuff 32 to the diaper 20, and includes embodiments wherein the barrier cuff 62 is a separate element having the proximal edge 64 directly or indirectly attached to the topsheet 38 (i.e., integral) or embodiments wherein the barrier cuff 62 is made from the same element or material as the topsheet 38 so that the proximal edge 64 is a continuous and undivided element of the topsheet (i.e., unitary). The barrier cuff 62 may alternatively be joined to the side flap 58, the backsheet 42, the absorbent core 44, the topsheet 38 or any combination of these or other elements of the diaper 20. In a preferred diaper 20, the barrier cuffs 62 are integral with the topsheet 38. The integral barrier cuff 62 is preferably formed by a single strip of material which is secured to the topsheet by adhesive 92, the distal edge 66 being formed by folding an end of the material back upon itself.

The distal edge 66 is preferably disposed inboard of the proximal edge 64 to present a more effective barrier against the flow of exudates. The distal edges 66 are maintained inboard of the proximal edges 64 by the adhesive means 78 so as to obviate their inversion. While the distal edges 66 may alternatively be disposed in other positions in relation to the proximal edges 64, such positions are not preferred.

The distal edge 66 is preferably not secured to any other element in at least the crotch region 26 of the diaper 20 so that it may be spaced away from the top surface 40 of the topsheet 38. The distal edge 66 is preferably spaced away from the top surface 40 of the topsheet 38 so that the barrier cuff 62 may form a channel 96 to enhance the containment of the article. As used herein, "spaced" includes embodiment wherein the distal edges 66 may assume one or more positions relative to the top surface 40 of the topsheet 38 including at some times assuming a position adjacent the top surface 40 of the topsheet 38. The distance between the distal edge 66 to the top surface 40 of the topsheet 38 is measured along a line drawn from the distal edge 66 to the closest part of the topsheet 38 when the distal edge 66 is positioned so as to be spaced away from the topsheet as far as possible. (i.e., in the elastically contracted position). Preferably, the distal edge 66 is spaced away from the topsheet 38 by a height of at least about 2 mm, and more preferably of from about 5 mm (about ¼") to about 10 mm (⅜").

The channel 96 is formed at least along the proximal and distal edges 64 and 66 and the inboard surface 68 of the barrier cuff 62. The channel 96 forms a barrier to the flow of exudates as they tend to move or float across the topsheet 38. Thus the channel 96 holds and contains exudates until the diaper 20 can be removed.

The barrier cuffs 62 may additionally be provided with absorbent means secured to or within the barrier cuff 62. The absorbent means absorb and contain exudates which contact the barrier cuff 62. The absorbent means may be any means which is capable of absorbing and retaining liquid and may have any size, shape, configuration or absorbent capacity. The absorbent means may be positioned to the barrier cuff 62 along the inboard surface 68 or within the barrier cuff 62. Preferably, the absorbent means is a layer of airfelt secured within the tunnel formed by the integral barrier cuff and secured along the entire length and width of the inboard surface 68 of the barrier cuff 62.

In addition, the barrier cuff 62 may be rendered liquid impermeable so as to prevent the strikethrough of body exudates. A liquid impermeable barrier cuff 62 retards the movement of liquid through the barrier cuff 62, thereby making it more leakage resistant. The barrier cuff 62 may be rendered liquid impermeable in any manner well known in the art such as selectively treating the barrier cuff, untreating the barrier cuff, or by securing a separate material to the barrier cuff.

The spacing means 76 for spacing the distal edge 66 away from the topsheet top surface 40 is any member which gathers, contracts, stiffens, shortens or otherwise acts on the barrier cuff 62 so as to cause a channel 96 to be formed along the barrier cuff 62 to provide a constraint against the leakage of exudates.

As shown in FIG. 1, the spacing means 76 preferably comprise spacing elastic member 77 secured adjacent the distal edge 66 inside of the barrier cuff 62. The spacing elastic member 77 is preferably secured to the barrier cuff 62 in an elastically contractible condition so that in a normally unrestrained configuration, the spacing elastic member 77 effectively contracts or gathers the barrier cuff 62. The spacing elastic member 77 can be secured to the barrier cuff 62 in an elastically contractible condition in at least two ways as is discussed in the above referenced U.S. Pat. No. 3,860,003 issued to K. B. Buell, In addition, the length of the spacing elastic member 77 in general is dictated by the diaper design. In the embodiment illustrated in FIG. 1, the spacing elastic member 77 extends essentially the entire length of the barrier cuff 36 in the crotch region 26, although other lengths are cognizable.

As shown in FIG. 3, the spacing elastic member 77 is associated with the barrier cuff 62 by securing it within the barrier cuff with elastic attachment means 94. While the spacing elastic members 77 may be secured to the barrier cuff 62 adjacent only the ends of the elastic spacing member 77, it is preferable to secure the entire length of the spacing elastic member 77 to the barrier cuff 62. The elastic attachment means 94 herein are preferably glue beads made of hot melt adhesive such as marketed by Findley Adhesives Incorporated, Elmgrove, Wis., as Findley Adhesives 581. A more detailed description of the manner in which the spacing elastic members 77 may be positioned and secured to the barrier cuff 62 can be found in U.S. Pat. No. 4,081,301, issued to Buell on Mar. 28, 1978, and in U.S. Pat. No. 4,253,461, issued to Strickland and Visscher on Mar. 3, 1981, both of which are incorporated herein by reference. It should also be noted that one or more spacing elastic members 77 can be used to elasticize each barrier cuff 62.

A spacing elastic member 77 which has been found suitable is an elastic strand having a cross section of 0.18 mm by 1.5 mm and made from natural rubber as available from Easthampton Rubber Company of Stewart, Va., under the trademark L-1900 Rubber Compound. Other suitable spacing elastic members 77 can be made from natural rubber, such as elastic tape sold under the trademark Fulflex 9211 by Fulflex Company of Scotland, N.C. The spacing elastic member 77 may also comprise any heat shrinkable elastic material as is well known in the art. Other suitable elastic materials may comprise a wide variety of materials as are well known in the art include elastomeric films, polyurethane films, elastomeric foams and formed elastic scrim.

In addition, the spacing elastic members 77 may take a multitude of configurations. For example, the width of the spacing elastic members 77 may be varied; the spacing elastic members may comprise a single strand or several parallel or non-parallel strands of elastic material; or the spacing elastic members 77 may be rectilinear or curvilinear. Still further, the spacing elastic members 77 may be affixed to the barrier cuff 62 in any of several ways which are well known in the art. For example, the spacing elastic members 77 may be ultrasonically bonded or heat sealed into the barrier cuff 62 using a variety of bonding patterns, or the spacing elastic members 77 may simply be glued to the barrie cuffs 62.

The spacing means 76 for spacing the distal edge 66 away from the topsheet top surface 40 may alternatively comprise several other elements. For example, the barrier cuff 62 may have stiffening means disposed in or on each barrier cuff 62. The stiffening means must be sufficiently stiff so that the distal edge 66 is spaced away from the topsheet top surface 40. Suitable materials for the stiffening means include foams, nonwoven fabrics, batting, polyethylene film, formed films, spray glues, foamed elastomerics, polyester, polyurethane, or a high loft material as is manufactured by Carolina Formed Fabrics.

The spacing means 77 may also comprise means for shortening the length of the distal edge 66 in comparison to the length of the edges of the diaper 20. The distal edge 66 can be shortened by making a fold or pleat in the distal edge 66. This fold or pleat is secured by any of the holding means well known to those of ordinary skill in the art, such as adhesives or heat sealing. Alternatively, a section may be cut out of the distal edge and the edges brought together to form a butt or lapp joint. The distal edge 66 may also be shortened by attaching a length of the distal edge 66 to the topsheet 38 at a position different from where the distal edge 66 would lie when the diaper 20 is in a flattened out condition. Other shortening techniques as are known in the art may also be used.

The adhesive means 78 for securing end portions 72 and 74 of the barrier cuff 62 closed are shown in FIGS. 1 and 2. The adhesive means 78 provide a more comfortable fit for the wearer and obviate inversion of the distal edges 66 of the barrier cuff 62 during application and use. Inversion is generally defined as the inboard disposed distal edge 66 turning outwardly when the diaper 20 is applied to the wearer. In a preferred embodiment as shown in FIGS. 1 and 2, such adhesive means 78 are disposed in the front waist region 22 and the back waist region 24 of the diaper in the front closure zone 80 and the back closure zone 82, respectively. The remaining portions of the barrier cuff 62 are not secured closed so that the distal edges 66 are left freely openable. In a preferred embodiment, the front closure zone 80 extends through the entire front waist region 22, while the back closure zone 82 extends through only a portion of the back waist region 24. This construction is preferred so as to create a channel 96 around the buttocks of the wearer to especially prevent leakage of loose fecal material.

The adhesive means 78 are preferably glue beads 79 consisting of hot melt adhesives such as marketed by Findley Adhesives Incorporated, Elmgrove, Wis., as Findley Adhesives 581.

FIG. 4 is a sectional view of the diaper 20 in its elastically contracted position prior to being placed on the wearer. The topsheet 38 is shown as the body contacting surface of the diaper 20, the backsheet 42 being disposed away from the body of the wearer. The gasketing cuffs 56 are shown to be gathered or contracted by the flap elastic members (not shown in FIG. 4). The diaper 20 is shown as having two barrier cuffs 62 extending adjacent to and inboard of the gasketing cuffs 56. The distal edges 66 are shown to be gathered and contracted by the spacing elastic members (not shown) in the crotch region 26 so as to provide a longitudinally extending channel 96 along the diaper 20. In addition, the ends 72 and 74 of the barrier cuff 62 are secured closed in the front and back closure zones 80 and 82, respectively, so as to provide comfort for the wearer, to obviate inversion of the barrier cuffs, and for ease of application of the diaper.

The diaper 20 is applied to a wearer, by positioning the back waist region 24 under the wearer's back, and drawing the remainder of the diaper 20 between the wearer's leg so that the front waist region 22 is positioned across the front of the person. The ends of the tape-tab fasteners 54 are then secured preferably to outwardly facing areas of the diaper 20. In this manner, the barrier cuffs 62 should be disposed in the crotch region of the wearer and should provide the dispositions and functions described hereinbefore. Once applied, the distal edges 66 of the barrier cuffs 62 extend through the groin areas and diverge upwardly along both of the buttocks of the wearer. Neither of the barrier cuffs 62 encircle the thighs of the wearer. However, the gasketing cuffs 56 will encircle the thighs and create a gasketing action against the thighs. The ends of the barrier cuff 62 are secured to the topsheet 38 to obviate the inversion of the barrier cuffs, for comfort for the wearer during application and use, and for ease of application.

Figure 5:
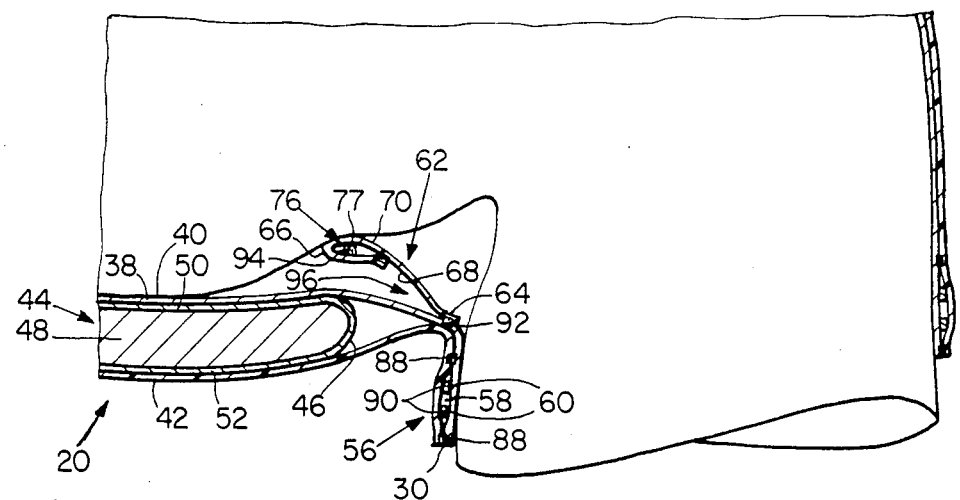
FIG. 5 is a fragmentary coronal view showing the diaper of FIG. 1 in place on a wearer.

FIG. 5 is a fragmentary coronal view showing a section of the diaper 20 of FIG. 1 in place on a wearer. (A coronal view is a frontal plane that passes through the long axis of the body.) As shown in FIG. 5, the gasketing cuffs 56 ride down on the legs and encircle the thighs of the wearer. The barrier cuffs 62 ride up on the legs and run through the crotch region and diverge upwardly over both the buttocks of the wearer. The barrier cuffs 62 do not encircle the thighs of the wearer. The distal edges 66 are spaced away from the top surface 40 of the topsheet 38 and lie against the perineum of the wearer. The barrier cuffs 62 are, therefore, pushed snuggly against the perineum of the wearer in the crotch region 26 of the diaper 20. The size of the channel 96 is enhanced by the resiliency of the absorbent core 44 because the core tends to push itself away from the perineum. This results in the diaper 20 having channels 96 extending along the crotch region of the wearer. Therefore, body exudates are restrained from penetrating beyond the barrier cuffs 62 because the channels 96 form a barrier to the flow of exudates.

Basically, without intending to limit the present invention, the present invention is a diaper that is especially useful and leakage resistant against loose fecal material, the improved containment characteristics being achieved in the following manner. As loose fecal material is dishcarged onto the topsheet 38, the material flows or floats on the top surface 40 of the topsheet 38. (Hereinafter referred to as surface material). The surface material moves from the point of discharge toward the longitudinal edges 30. Surface material will contact the barrier cuff 32 along the inboard surface 68. In normal use, gravitational forces will tend to cause the surface material to collect in the channel 96 formed by the standing barrier cuff 62; the material being held in the channels 96 until the diaper 20 can be removed. Improved containment is achieved because surface material would have to flow up the channel 96, which direction is substantially directly against the force of gravity when the wearer is in an upright position, in order to penetrate and flow over the distal edges 66 of the barrier cuffs 62. However, should such material flow beyond the barrier cuffs 62, it is retarded from leaking out of the diaper 20 by the gasketing effect achieved by the gasketing cuffs 56, as they draw and gather the side flaps 58 about the legs of the wearer, thereby providing a second and independent effective barrier against leakage so as to further prevent the soiling of adjacent garments.

Figure 6:
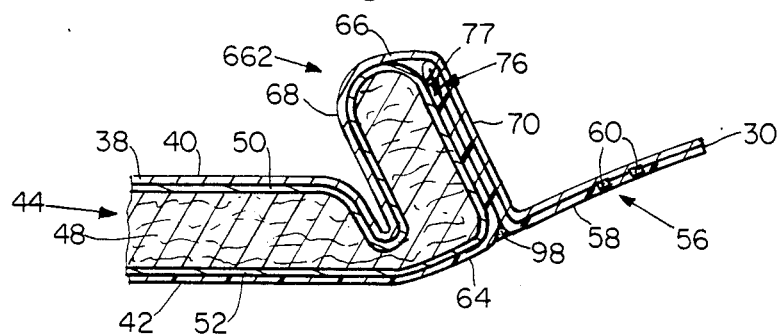
FIG. 6 is a fragmentary sectional view of an alternative embodiment of the present invention.

FIG. 6 is a sectional view of an alternative barrier cuff 662 of the diaper 20 of the present invention. A unitary barrier cuff 662 is formed by pleating the entire diaper structure (i.e., the backsheet 42, the absorbent core 44, and the topsheet 38.) After pleating the structure, the proximal edge 64 of the barrier cuff 662 are secured together by adhesive 98. The barrier cuff 662 may preferably having spaced means such as spacing elastic members 77 secured within the barrier cuff 662 to elasticize the distal edges 66 of the barrier cuff 662 so as to space the distal edges 66 away from the top surface 40 of the topsheet 38.

Figure 7:
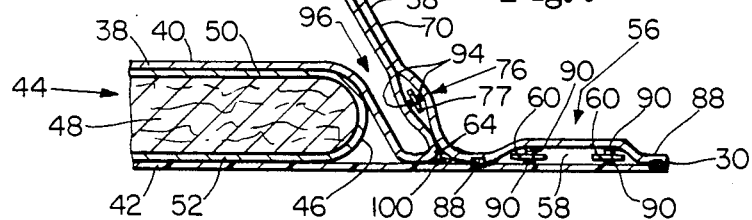
FIG. 7 is a fragmentary sectional view of a further alternative embodiment of the present invention.

FIG. 7 is another fragmentary sectional view of an alternative embodiment of the present invention.

A unitary barrier cuff 762 is formed by U-folding or pleating the topsheet of the diaper 20 of the present invention. The topsheet is folded upon itself to form a distal edge 66; spacing elastic members 77 are secured within the tunnel formed in the distal edge 66. The proximal edge 64 is secured by adhesive attachment means 100 such as a glue bead made of hot melt adhesives.

While particular embodiment of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An integral disposable absorbent article comprising:
    a liquid pervious topsheet; a liquid impervious backsheet associated with said topsheet;
    an absorbent core disposed between said topsheet and said backsheet;
    an elastically contractible gasketing cuff disposed adjacent to an edge of the absorbent article;
    a barrier cuff having a proximal edge and a distal edge, said barrier cuff disposed inboard of said gasketing cuff; and
    spacing means associated with said barrier cuff for spacing said distal edge away from the top surface of said topsheet.

2. The integral disposable absorbent article of claim 1 wherein said spacing means comprises a spacing elastic member.

3. The integral disposable absorbent article of claim 1 wherein said spacing means comprises a stiffening means.

4. The integral disposable absorbent article of claim 1 wherein said spacing means comprises a means for shortening the length of said barrier cuff in comparison to the length of the edge of the absorbent article.

5. An integral disposable absorbent article having a front waist region, a crotch region and a back waist region, said absorbent article comprising:
    a liquid pervious topsheet;
    a liquid impervious backsheet associated with said topsheet;
    an absorbent core disposed between said topsheet and said backsheet;
    an elastically contractible gasketing cuff disposed adjacent each longitudinal edge of the absorbent article in at least the crotch region;
    a barrier cuff disposed adjacent each of said gasketing cuffs, each of said barrier cuffs having a proximal edge and a distal edge, said proximal edge disposed laterally inboard of said gasketing cuff;
    a spacing means associated with each of said barrier cuffs, for spacing said distal edge away from the top surface of said topsheet, whereby a channel is formed to improve the containment characteristics of the article.

6. The integral disposable absorbent article of claim 5 wherein said spacing means comprises a spacing elastic member.

7. The integral disposable absorbent article of claim 6 wherein said spacing elastic member is an elastic strand.

8. The integral disposable absorbent article of claim 6 wherein said spacing elastic member is a heat shrinkable elastic material.

9. The integral disposable absorbent article of claim 5 wherein said spacing means comprises a stiffening means.

10. The integral disposable absorbent article of claim 5 wherein said spacing means comprises a means for shortening the length of said barrier cuff in comparison to the length of the longitudinal edge of the absorbent article.

11. The integral disposable absorbent article of claim 5 wherein said barrier cuff is integral with said topsheet.

12. The intgral disposable absorbent article of claim 11 wherein said barrier cuff is a polypropylene material.

13. The integral disposable absorbent article of claim 11 wherein said barrier cuff is liquid impermeable.

14. The integral disposable absorbent article of claim 5 wherein said barrier cuff is unitary with said topsheet.

15. The integral disposable absorbent article of claim 5 wherein said barrier cuff is unitary with said topsheet, backsheet and absorbent core.

16. The absorbent article of claim 5 additionally comprising adhesive means disposed adjacent each of the ends of said barrier cuff for securing closed a portion of said barrier cuff, a portion of said distal edge in at least the crotch region remaining free from attachment so as to be spaced away from said topsheet.

17. The integral disposable absorbent article of claim 5 wherein said barrier cuff is liquid impermeable.

18. The integral disposable absorbent article of claim 5 wherein said barrier cuff additionally comprises an absorbent means.

19. An integral disposable absorbent article having a front waist region, a crotch region and a back waist region, said absorbent article comprising:
 a liquid pervious topsheet;
 a liquid impervious backsheet associated with said topsheet;
 an absorbent core having side edges, said absorbent core disposed between said topsheet and said backsheet;
 an elastically contractible gasketing cuff disposed adjacent each longitudinal edge of the absorbent article, each gasketing cuff comprising a flexible side flap extending from and along said side edge of said absorbent core in at least the crotch region of the absorbent article, and a flap elastic member secured to said side flap in an elastically contractible condition, whereby said elastically contractible gasketing cuff forms an effective barrier about a wearer's legs;
 a barrier cuff disposed adjacent each of said gasketing cuffs in at least the crotch region, each of said barrier cuffs having a proximal edge and a distal edge, said proximal edge disposed in said side flap between said flap elastic member and said side edge of said absorbent core in at least the crotch region, said distal edge being free from attachment in at least the crotch region; and
 a spacing elastic member secured to said barrier cuff for elasticizing said barrier cuff so that said distal edge is spaced away from the top surface of said topsheet, whereby a channel is formed;
 said elastically contractible gasketing cuff and said barrier cuff presenting an effective means against the soiling of a wearer's garments.

20. The aabsorbent article of claim 19 additionally comprising adhesive means, disposed adjacent each end of each of said barrier cuffs in the front and back waist regions, for securing closed said barrier cuff, said distal edge remaining free to be spaced away from the top surface of said topsheet in at least said crotch region.

21. The integral disposable absorbent article of claim 19 wherein said barrier cuff is liquid impermeable.

22. The integral disposable absorbent article of claim 19 wherein said flap elastic member is curvilinear.

23. The integral disposable absorbent article of claim 19 wherein said barrier cuff is integral with said topsheet.

24. The integral disposable absorbent article of claim 19 wherein said barrier cuff is integral with said side flap.

25. The integral disposable absorbent article of claim 24 wherein said barrier cuff is liquid impermeable.

26. An integral disposable absorbent article comprising:
 a liquid pervious topsheet;
 a liquid impervious backsheet associated with said topsheet;
 an absorbent core disposed between said topsheet and said backsheet;
 an elastically contractible gasketing cuff disposed adjacent to an edge of the absorbent article;
 a barrier cuff having a proximal edge and a distal edge, said proximal edge disposed adjacent said gasketing cuff and said distal edge disposed inboard of said proximal edge; and
 a spacing means associated with said barrier cuff for spacing said distal edge away from the top surface of said topsheet.

27. The integral disposable absorbent article of claim 26 wherein said barrier cuff is liquid impermeable.

28. The integral disposable absorbent article of claim 27 wherein said proximal edge is disposed inboard of said gasketing cuff.

* * * * *

UNITED STATES PATENT AND TRADEMARK OFFICE
CERTIFICATE OF CORRECTION

PATENT NO. : 4,695,278
DATED : September 22, 1987
INVENTOR(S) : Michael I. Lawson It is certified that error appears in the above-identified patent and that said Letters Patent is hereby corrected as shown below:

Cover Page, References Cited, add "3,452,753 7/69 Sanford"

Column 3, Line 56, delete "peripher" and insert ---perimeter---.

Column 4, Line 18, delete "front" and "22".

Column 5, Line 13, delete "liquid" and insert ---liquids---.

Column 5, Line 52, delete "84" and insert ---48---.

Column 6, Line 6, delete "dimensions" and insert ---dimension---.

Column 10, Line 39, delete "liquid" and insert ---liquids---.

Column 11, Line 57, delete "barrie" and insert ---barrier---.

Column 13, Line 68, delete "having spaced" and insert ---have spacing---.

Column 14, line 5, delete "an" and insert ---a further---.

Signed and Sealed this

Nineteenth Day of April, 1988

Attest:

DONALD J. QUIGG

Attesting Officer

Commissioner of Patents and Trademarks

(12) REEXAMINATION CERTIFICATE (4421st)
United States Patent
Lawson

(10) Number: US 4,695,278 C1
(45) Certificate Issued: Aug. 28, 2001

(54) ABSORBENT ARTICLE HAVING DUAL CUFFS

(75) Inventor: Michael I. Lawson, Cincinnati, OH (US)

(73) Assignee: The Procter & Gamble Company, Cincinnati, OH (US)

Reexamination Request:
No. 90/005,347, Apr. 26, 1999

Reexamination Certificate for:
| | |
|---|---|
| Patent No.: | 4,695,278 |
| Issued: | Sep. 22, 1987 |
| Appl. No.: | 06/786,926 |
| Filed: | Oct. 11, 1985 |

Certificate of Correction issued Apr. 19, 1988.

(51) Int. Cl.⁷ .......................... A61F 13/15; A61F 13/20
(52) U.S. Cl. ......................... 604/385.27; 604/385.24
(58) Field of Search ............................. 604/385.1, 385.2

(56) References Cited

U.S. PATENT DOCUMENTS

| | | |
|---|---|---|
| Re. 26,151 | 1/1967 | Duncan et al. . |
| Re. 33,106 | 11/1989 | Beckestrom . |
| Re. 34,920 | 4/1995 | Aziz et al. . |
| 2,545,674 | 3/1951 | Ralph . |
| 2,575,164 | 11/1951 | Donovan . |
| 2,714,889 | 8/1955 | Chambers . |
| 2,745,405 | 5/1956 | Landy et al. . |
| 2,862,251 | 12/1958 | Kalwaites . |
| 2,893,393 | 7/1959 | Pressley . |
| 2,916,037 | 12/1959 | Hansen . |
| 3,081,514 | 3/1963 | Griswold . |
| 3,081,515 | 3/1963 | Griswold . |
| 3,364,931 | 1/1968 | Hirsch . |
| 3,386,442 | 6/1968 | Sabee . |
| 3,452,753 | 7/1969 | Sanford . |
| 3,485,706 | 12/1969 | Evans . |
| 3,530,859 | 9/1970 | Helmowitz . |
| 3,561,446 | 2/1971 | Jones, Sr. . |
| 3,570,493 | 3/1971 | Olsson . |
| 3,572,342 | 3/1971 | Lindquist et al. . |

(List continued on next page.)

FOREIGN PATENT DOCUMENTS

| | | |
|---|---|---|
| 188667 | 2/1957 | (AT) . |
| 45217/85 | 2/1986 | (AU) . |
| 1070779 | 12/1959 | (DE) . |
| 0027303 | 4/1981 | (EP) . |
| 0070584 | 1/1983 | (EP) . |
| 0091412 | 10/1983 | (EP) . |
| 2561078 | 9/1965 | (FR) . |

(List continued on next page.)

OTHER PUBLICATIONS

Patent Interference No. 102,274.

*Primary Examiner*—Mark O. Polutta

(57) ABSTRACT

An integral disposable absorbent article such as a diaper having a liquid pervious topsheet, a liquid impervious backsheet, an absorbent core disposed between the topsheet and the backsheet, at least one elastically contractible gasketing cuff, and at least one barrier cuff. The barrier cuff has a proximal edge and a distal edge. The absorbent article is additionally provided with spacing means for spacing the distal edge away from the top surface of the topsheet. In addition, adhesive means secure the end portions of the barrier cuff closed. A channel is formed between the proximal and distal edges in at least the crotch region because the distal edge is spaced away from the topsheet top surface.

When the diaper embodiment of the present invention is applied to a wearer, the barrier cuff rides up along the inner thighs and the perineum of the wearer in the crotch region and along the buttocks in the back waist region. Leakage prevention is enhanced because body exudates which are not immediately absorbed by the absorbent core contact the barrier cuff and are contained and held within the channel so that they do not wick out of the diaper or flow out of the gaps between the diaper and the legs or waist of the wearer. Additionally, should such exudates flow beyond the barrier cuff, leakage is further enhanced by the gasketing cuff because it forms an additional liquid impervious barrier about the leg or waist of the wearer.

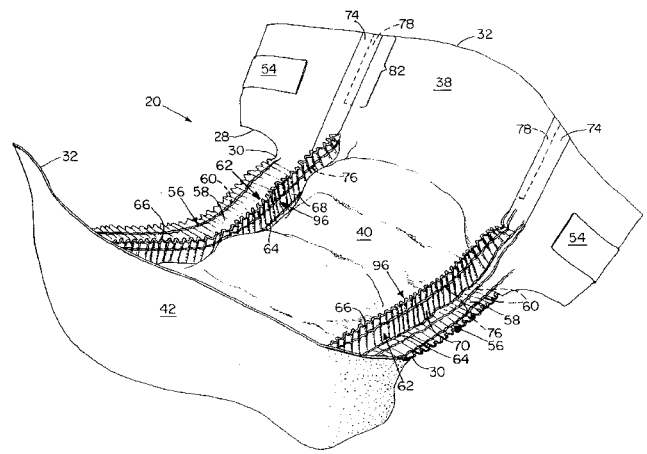

U.S. PATENT DOCUMENTS

| | | |
|---|---|---|
| 3,593,716 | 7/1971 | Vogt . |
| 3,612,055 | 10/1971 | Mesek et al. . |
| 3,658,063 | 4/1972 | Schaar . |
| 3,658,064 | 4/1972 | Pociluyko . |
| 3,663,348 | 5/1972 | Liloia et al. . |
| 3,667,466 | 6/1972 | Ralph . |
| 3,744,494 | 7/1973 | Marsan . |
| 3,759,261 | 9/1973 | Wang . |
| 3,769,978 | 11/1973 | DeNight et al. . |
| 3,771,524 | 11/1973 | Ralph . |
| 3,807,402 | 4/1974 | Miller et al. . |
| 3,848,594 | 11/1974 | Buell . |
| 3,848,598 | 11/1974 | Mesek . |
| 3,860,002 | 1/1975 | Kolbach . |
| 3,860,003 | 1/1975 | Buell . |
| 3,885,568 | 5/1975 | Schaar . |
| 3,886,941 | 6/1975 | Duane et al. . |
| 3,900,031 | 8/1975 | Endres et al. . |
| 3,906,952 | 9/1975 | Zamist . |
| 3,913,578 | 10/1975 | Schaar . |
| 3,920,017 | 11/1975 | Karami . |
| 3,929,134 | 12/1975 | Karami . |
| 3,943,930 | 3/1976 | Schaar . |
| 3,965,906 | 6/1976 | Karami . |
| 3,978,861 | 9/1976 | Schaar . |
| 3,999,547 | 12/1976 | Hernandez . |
| 3,999,548 | 12/1976 | Hernandez . |
| 4,040,423 | 8/1977 | Jones, Sr. . |
| 4,041,950 | 8/1977 | Jones, Sr. . |
| 4,041,951 | 8/1977 | Sanford . |
| 4,044,769 | 8/1977 | Papajohn . |
| 4,050,462 | 9/1977 | Woon et al. . |
| 4,081,301 | 3/1978 | Buell . |
| 4,090,515 | 5/1978 | Karami . |
| 4,094,319 | 6/1978 | Joa . |
| 4,108,179 | 8/1978 | Schaar . |
| 4,173,612 | 11/1979 | Kelly . |
| 4,210,143 | 7/1980 | De Jonckheere . |
| 4,246,900 | 1/1981 | Schröder . |
| 4,253,461 | 3/1981 | Strickland et al. . |
| 4,259,958 | 4/1981 | Goodbar . |
| 4,305,990 | 12/1981 | Kelly . |
| 4,319,572 | 3/1982 | Widlund et al. . |
| 4,326,528 | 4/1982 | Ryan et al. . |
| 4,333,782 | 6/1982 | Pieniak . |
| 4,337,771 | 7/1982 | Pieniak et al. . |
| 4,341,216 | 7/1982 | Obenour . |
| 4,352,355 | 10/1982 | Mesek et al. . |
| 4,381,782 | 5/1983 | Mazurak et al. . |
| 4,395,215 | 7/1983 | Bishop . |
| 4,397,645 | 8/1983 | Buell . |
| 4,402,688 | 9/1983 | Julemont . |
| 4,402,690 | 9/1983 | Redfern . |
| 4,413,996 | 11/1983 | Taylor . |
| 4,425,127 | 1/1984 | Suzuki et al. . |
| 4,430,086 | 2/1984 | Repke . |
| 4,437,860 | 3/1984 | Sigl et al. . |
| 4,490,148 | 12/1984 | Beckeström . |
| 4,496,360 | 1/1985 | Joffe et al. . |
| 4,500,316 | 2/1985 | Damico . |
| 4,527,989 | 7/1985 | Karami . |
| 4,578,073 | 3/1986 | Dysart et al. . |
| 4,579,556 | 4/1986 | McFarland . |
| 4,591,523 | 5/1986 | Thompson . |
| 4,597,760 | 7/1986 | Buell . |
| 4,597,761 | 7/1986 | Buell . |
| 4,601,717 | 7/1986 | Blevins . |
| 4,623,342 | 11/1986 | Ito . |
| 4,636,207 | 1/1987 | Buell . |
| 4,650,483 | 3/1987 | Joffe . |
| 4,657,539 | 4/1987 | Hasse . |
| 4,662,877 | 5/1987 | Williams . |
| 4,695,278 | 9/1987 | Lawson .......................... 604/385 A |
| 4,704,115 | 11/1987 | Buell . |
| 4,704,116 | 11/1987 | Enloe . |
| 4,743,246 | 5/1988 | Lawson . |
| 4,747,991 | 5/1988 | Bishop . |
| 4,753,646 | 6/1988 | Enloe . |
| 4,808,178 | 2/1989 | Aziz et al. . |
| 4,846,823 | 7/1989 | Enloe . |
| 4,900,317 | 2/1990 | Buell . |
| 4,909,803 | 3/1990 | Aziz et al. . |
| 5,085,654 | 2/1992 | Buell . |
| 5,413,570 | 5/1995 | Enloe . |
| 5,415,644 | 5/1995 | Enloe . |
| 5,599,338 | 2/1997 | Enloe . |
| B1 4,636,207 | 11/1989 | Buell . |

FOREIGN PATENT DOCUMENTS

| | | |
|---|---|---|
| 2063794 | 7/1971 | (FR) . |
| 358765 | 10/1931 | (GB) . |
| 667483 | 3/1952 | (GB) . |
| 790062 | 2/1958 | (GB) . |
| 1543915 | 4/1979 | (GB) . |
| 2063677A | 6/1981 | (GB) . |
| 2101468A | 1/1983 | (GB) . |
| 2130491A | 6/1984 | (GB) . |
| 2149289A | 6/1985 | (GB) . |
| 2159693A | 12/1985 | (GB) . |
| 2161059A | 1/1986 | (GB) . |
| 33-9632 | 7/1958 | (JP) . |
| 36-7548 | 4/1961 | (JP) . |
| 39-33810 | 11/1964 | (JP) . |
| 39-33813 | 11/1964 | (JP) . |
| 40-1548 | 1/1965 | (JP) . |
| 40-11543 | 4/1965 | (JP) . |
| 40-21930 | 7/1965 | (JP) . |
| 41-17377 | 8/1966 | (JP) . |
| 41-18031 | 8/1966 | (JP) . |
| 41-18359 | 8/1966 | (JP) . |
| 42-7943 | 4/1967 | (JP) . |
| 42-11718 | 6/1967 | (JP) . |
| 52-40267 | 10/1977 | (JP) . |
| 54-10050 | 1/1979 | (JP) . |
| 57-89602 | 6/1982 | (JP) . |
| 58-105405 | 7/1983 | (JP) . |
| 59-25741 | 2/1984 | (JP) . |
| 59-28508 | 2/1984 | (JP) . |
| 59-76903 | 5/1984 | (JP) . |
| 59-146651 | 8/1984 | (JP) . |
| 60-104502 | 6/1985 | (JP) . |
| 196521 | 6/1983 | (NZ) . |

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 3, 9, 13, 17, 18, 21, 25, 27 and 28 is confirmed.

Claims 1, 2, 4–8, 10–12, 14–16, 19, 20, 22–24 and 26 were previously cancelled.

New claims 29–42 are added and determined to be patentable.

*29. The integral disposable absorbent article of claim 27 wherein said spacing means comprises several elastic strands.*

*30. The integral disposable absorbent article of claim 29 wherein the width of said elastic strands is varied.*

*31. The integral disposable absorbent article of claim 27 wherein said gasketing cuff comprises a side flap, and an elastic strand associated with said side flap to gather or contract said side flap.*

*32. The integral disposable absorbent article of claim 31 wherein said barrier cuff is joined to said side flap.*

*33. The integral disposable absorbent article of claim 32 wherein said elastic strand is disposed adjacent said proximal edge.*

*34. The integral disposable absorbent article of claim 33 wherein said spacing means comprises several elastic strands.*

*35. The integral disposable absorbent article of claim 34 wherein the width of said elastic strands is varied.*

*36. The integral disposable absorbent article of claim 32 wherein said side flap comprises an extension of said backsheet.*

*37. The integral disposable absorbent article of claim 17, 21, 25, 27 or 28 wherein said barrier cuff comprises a nonwoven.*

*38. The integral disposable absorbent article of claim 17, 21, 25, 27 or 28 wherein said barrier cuff comprises a plastic film.*

*39. The integral disposable absorbent article of claim 21 wherein said barrier cuff is integral with said side flap.*

*40. The integral disposable absorbent article of claim 17, 21, 27 or 28 wherein said barrier cuff is integral with said topsheet.*

*41. The integral disposable absorbent article of claim 17, 21, 27 or 28 wherein said barrier cuff is integral with said backsheet.*

*42. The integral disposable absorbent article of claim 17, 21, 25, 27 or 28 additionally comprising adhesive means disposed adjacent each of the ends of said barrier cuff for securing closed a portion of said barrier cuff, a portion of said distal edge in at least the crotch region remaining free from attachment so as to be spaced away from said topsheet.*

\* \* \* \* \*